United States Patent

Armitage et al.

[11] Patent Number: 5,854,257
[45] Date of Patent: Dec. 29, 1998

[54] NAPHTHYRIDINONE DERIVATIVES

[75] Inventors: Bernard John Armitage; Bruce William Leslie, both of Nottingham, Great Britain

[73] Assignee: Knoll Aktiengesellschaft, Ludwigschafen, Germany

[21] Appl. No.: 809,580

[22] PCT Filed: Sep. 26, 1995

[86] PCT No.: PCT/EP95/03808

§ 371 Date: Mar. 24, 1997

§ 102(e) Date: Mar. 24, 1997

[87] PCT Pub. No.: WO96/11199

PCT Pub. Date: Apr. 18, 1996

[30] Foreign Application Priority Data

Oct. 6, 1994 [GB] United Kingdom ................ 9420168.8

[51] Int. Cl.⁶ ........................ A61K 31/435; C07D 471/04
[52] U.S. Cl. ........................................... 514/300; 546/123
[58] Field of Search ................ 546/123; 514/300

[56] References Cited

U.S. PATENT DOCUMENTS

| | | | |
|---|---|---|---|
| 4,128,649 | 12/1978 | Hardtmann | 424/256 |
| 4,215,123 | 7/1980 | Scotese et al. | 424/256 |

FOREIGN PATENT DOCUMENTS

| | | |
|---|---|---|
| 018 735 | 11/1980 | European Pat. Off. . |
| 452 873 | 10/1991 | European Pat. Off. . |
| 52116495 | 9/1977 | Japan . |
| 93/13097 | 7/1993 | WIPO . |
| 95/07909 | 3/1995 | WIPO . |

OTHER PUBLICATIONS

*Pat. Abst. of Japan*, vol. 16, No. 560, Dec. 2, 1992 (English abstract of JP 4217981, Aug. 7, 1992).
*J. Med. Chem.*, vol. 31, 1988, pp. 2108–2121.
*J. Med. Chem.*, vol. 30, 1987, pp. 2270–2277.

*Primary Examiner*—Bernard Dentz
*Attorney, Agent, or Firm*—Keil & Weinkauf

[57] ABSTRACT

Compounds of formula I

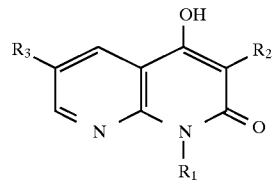

including pharmaceutically acceptable salts thereof in which $R_1$ represents a phenyl $C_{1-6}$ alkyl group (in which the phenyl ring is optionally substituted by one or more of the following: halo, a $C_{1-4}$ alkyl group, a $C_{1-4}$ alkoxy group, hydroxy or trifluoromethyl) and the alkyl chain is optionally substituted by one or more $C_{1-2}$ alkyl groups; $R_2$ represents a $C_{2-6}$ alkoxycarbonyl group; and $R_3$ represents hydrogen or halo are disclosed, which are antirheumatic agents and are useful as modulators of cytokine synthesis, immunomodulatory agents, antiinflammatory agents and anti-allergic agents. Compositions containing these compounds and processes to make these compounds are also disclosed.

7 Claims, No Drawings

NAPHTHYRIDINONE DERIVATIVES

This application is a 371 of PCT/EP95/03808 filed Sep. 26, 1995.

The present invention relates to therapeutic agents and, in particular, to substituted alkyl 1-phenylalkyl-4-hydroxy-2-oxo-1,8-naphthyridine-3-carboxylates, to processes for their preparation, to pharmaceutical compositions containing them and to their therapeutic activity as anti-rheumatic agents.

Rheumatoid arthritis is currently treated with anti-inflammatory agents, which alleviate the symptoms but do not affect the progression of the condition, or with disease-modifying antirheumatic drugs e.g. gold compounds, D-penicillamine, sulphasalazine, azathioprine and methotrexate. However, most disease-modifying antirheumatic drugs are associated with side-effects, often of a serious nature. This means that such drugs are often only used as a last resort in the most serious cases. Consequently a need exists for a less toxic, disease-modifying, antirheumatic drug which may be administered orally.

EP 452,873 discloses the use of substituted 1-aryl-1,8-naphthyridine-3-carboxamides of formula A

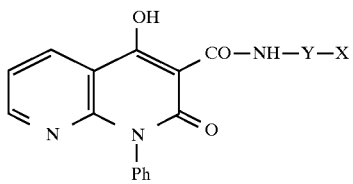

in which X represents hydrogen, a $C_{1-6}$ alkyl group, aralkyl, aryl, an aromatic heterocyclic group etc. and Y represents a single bond or alkylene, as antiinflammatory agents which are useful in the treatment of rheumatoid arthritis.

Japanese Patent Application 52-116495 (1977) discloses compounds of formula B

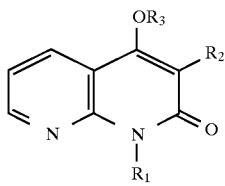

in which $R_1$ represents an alkyl group (optionally substituted), an alkenyl group or an aryl group; $R_2$ represents, hydrogen, an alkyl group (optionally substituted) or an aryl group and $R_3$ represents hydrogen or an acyl group, which allegedly possess analgesic, antiinflammatory, central nervous system depressant and diuretic effects. There is no suggestion in this document that the compounds have any anti-rheumatic activity.

U.S. Pat. No. 4,128,649 discloses compounds of formula C

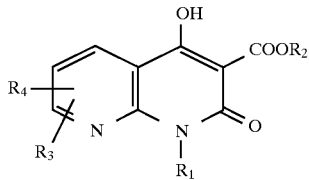

wherein $R_1$ represents hydrogen, alkyl, cycloalkyl, aryl, arylalkyl etc; $R_2$ represents hydrogen, a $C_{1-4}$ alkyl group, a $C_{3-6}$ alkenyl group or a $C_{3-6}$ alkynyl group; $R_3$ and $R_4$ independently represent hydrogen or a $C_{1-4}$ alkyl group and/or salts thereof. Ethyl 1-benzyl-4-hydroxy-7-methyl-2-oxo-1,2-dihydro-1,8-naphthyridine-3-carboxylate is specifically named. The use of these compounds as anti-allergic agents is also disclosed. There is no suggestion in this document that the compounds have any anti-rheumatic activity.

U.S. Pat. No. 4,215,123 discloses a method of treating peptic ulcers comprising the administration of a compound of formula D

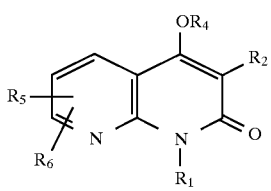

wherein $R_1$ represents hydrogen, a $C_{1-6}$ alkyl group, a $C_{7-9}$ aralkyl group etc; $R_2$ represents hydrogen, a $C_{2-7}$ alkoxycarbonyl group, carboxy, carbamoyl, $C_{2-7}$ N-alkylcarbamoyl etc; $R_4$ is hydrogen or a $C_{1-6}$ alkyl group and $R_5$ and $R_6$ are independently hydrogen or a $C_{1-6}$ alkyl group or an alkali metal salt thereof. Ethyl 1-benzyl-1,2-dihydro-4-hydroxy-7-methyl-2-oxo-1,8-naphthyridine-3-carboxylate is specifically exemplified. There is no suggestion in this document that the compounds have any anti-rheumatic activity.

The structure activity relationships of a series of 4-hydroxy-1-phenyl-1,8-naphthyridin-2(1H)-ones, which are antiallergy agents, is reported in J. Med. Chem. 1988. 31. 2108–2121. 1-Benzyl-3-butyl-4-hydroxy-1,8-naphthyridin-2(1H)-one is disclosed as being inactive.

The present invention provides compounds of formula I

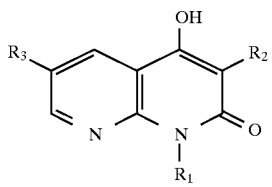

including pharmaceutically acceptable salts thereof in which
$R_1$ represents a phenyl $C_{1-6}$ alkyl group (in which the phenyl ring is optionally substituted by one or more of the following: halo, a $C_{1-4}$ alkyl group, a $C_{1-4}$ alkoxy group, hydroxy or trifluoromethyl) and the alkyl chain is optionally substituted by one or more $C_{1-2}$ alkyl groups;
$R_2$ represents a $C_{2-6}$ alkoxycarbonyl group; and
$R_3$ represents hydrogen or halo.

In a preferred group of compounds of formula I, $R_3$ represents halo.

It will be understood that a group containing a chain of 3 or more carbon atoms may be straight or branched, for example, propyl includes n-propyl and isopropyl and butyl includes n-butyl, sec-butyl, isobutyl and tert-butyl. The total number of carbon atoms is specified for certain substituents, for example $C_{2-6}$ alkoxycarbonyl refers to an alkoxycarbonyl group having from two to six carbon atoms. The term "halo" covers fluoro, chloro or bromo.

A compound of formula I will generally exist in equilibrium with its other tautomeric forms. It is to be understood that all tautomeric forms of the compounds of formula I, as well as mixtures thereof, are included within the scope of the present invention.

In a more preferred group of compounds of formula I, $R_1$ represents phenethyl or a benzyl group optionally substituted in the phenyl ring by one or more of the following: a $C_{1-4}$ alkoxy group or halo; $R_2$ represents a $C_{2-4}$ alkoxycarbonyl group and $R_3$ represents hydrogen or halo.

Preferably $R_1$ represents benzyl, 4-chlorobenzyl, 4-methoxybenzyl or phenethyl. More preferably $R_1$ represents benzyl or 4-chlorobenzyl. Most preferably $R_1$ represents benzyl.

Preferably $R_2$ represents methoxycarbonyl, ethoxycarbonyl or propoxycarbonyl. More preferably $R_2$ represents ethoxycarbonyl.

Preferably $R_3$ represents hydrogen, chloro, bromo or fluoro. More preferably $R_3$ represents hydrogen or chloro. Most preferably $R_3$ represents chloro.

Specific compounds of formula I are:

ethyl 1-benzyl-6-chloro-4-hydroxy-2-oxo-1,2-dihydro-1,8-naphthyridine-3-carboxylate;

ethyl 1-benzyl-4-hydroxy-2-oxo-1,2-dihydro-1,8-naphthyridine-3-carboxylate;

ethyl 1-(4-chlorobenzyl)-4-hydroxy-2-oxo-1,2-dihydro-1,8-naphthyridine-3-carboxylate;

ethyl 6-chloro-4-hydroxy-1-(4-methoxybenzyl)-2-oxo-1,2-dihydro-1,8-naphthyridine-3-carboxylate; and ethyl 4-hydroxy-2-oxo-1-phenethyl-1,2-dihydro-1,8-naphthyridine-3-carboxylate;

and pharmaceutically acceptable salts thereof.

Compounds of formula I may contain one or more chiral centres and exist in different optically active forms. When a compound of formula I or a salt thereof contains a single chiral centre it may exist in two enantiomeric forms. The present invention includes individual enantiomers and mixtures of those enantiomers. The enantiomers may be obtained by methods known to those skilled in the art. Such methods typically include resolution via formation of diastereoisomeric salts or complexes which may be separated, for example, by crystallisation; resolution via formation of diastereoisomeric derivatives or complexes which may be separated, for example, by crystallisation, gas-liquid or liquid chromatography; selective reaction of one enantiomer by reaction with an enantiomer-specific reagent, for example, enzymatic esterification, oxidation or reduction, followed by separation of the modified and unmodified enantiomers; or gas-liquid or liquid chromatography in a chiral environment, for example on a chiral support such as silica with a bound chiral ligand or in the presence of a chiral solvent. It will be appreciated that where the desired enantiomer is converted into another chemical entity by one of the separation processes described above, at least one further step will subsequently be required to liberate the desired enantiomeric form. Alternatively, specific enantiomers may be synthesised by asymmetric synthesis using optically active reagents, substrates, catalysts or solvents, or by converting one enantiomer into the other by asymmetric transformation.

When a compound of formula I or a salt thereof contains more than one chiral centre it may exist in diastereoisomeric forms. The diastereoisomeric pairs may be separated by methods known to those skilled in the art, for example, chromatography or crystallisation and the individual enantiomers within each pair may be separated as described above. The present invention includes each diastereoisomer of compounds of formula I and mixtures thereof.

Some compounds of formula I may exist in the form of solvates, for example, hydrates, which also fall within the scope of the present invention.

The compounds of formula I may form organic or inorganic salts, for example, the compounds of formula I may form acid addition salts with inorganic or organic acids, e.g. hydrochloric acid, hydrobromic acid, fumaric acid, tartaric acid, citric acid, sulphuric acid, hydriodic acid, maleic acid, acetic acid, succinic acid, benzoic acid, pamoic acid, palmitic acid, dodecanoic acid and acidic amino acids such as glutamic acid. Some compounds of formula I may form base addition salts, for example, with alkali metal hydroxides for example sodium hydroxide, with aminoacids for example, lysine or arginine or with organic bases, for example meglumine. It will be appreciated that such salts, provided they are pharmaceutically acceptable may be used in therapy in place of the corresponding compounds of formula I. Such salts are prepared by reacting the compound of formula I with a suitable acid or base in a conventional manner. Such salts may also exist in form of solvates (for example, hydrates).

Certain compounds of formula I or salts thereof may exist in more than one crystal form and the present invention includes each crystal form and mixtures thereof.

The present invention also provides pharmaceutical compositions containing a therapeutically effective amount of a compound of formula I including pharmaceutically acceptable salts thereof together with a pharmaceutically acceptable diluent or carrier. Such pharmaceutical formulations may be used in the treatment of rheumatic diseases for example rheumatoid arthritis or osteoarthritis.

As used hereinafter, the term "active compound" denotes a compound of formula I including pharmaceutically acceptable salts thereof. In therapeutic use, the active compound may be administered orally, rectally, parenterally, topically, ocularly, aurally, nasally, intravaginally or to the buccal cavity, to give a local and/or systemic effect. Thus the therapeutic compositions of the present invention may take the form of any of the known pharmaceutical compositions for such methods of administration. The compositions may be formulated in a manner known to those skilled in the art so as to give a controlled release, for example rapid release or sustained release, of the compounds of the present invention. Pharmaceutically acceptable carriers suitable for use in such compositions are well known in the art of pharmacy. The compositions of the invention may contain 0.1–99% by weight of active compound. The compositions of the invention are generally prepared in unit dosage form. Preferably the unit dosage of active ingredient is 1–500 mg. The excipients used in the preparation of these compositions are the excipients known in the pharmacist's art.

Compositions for oral administration are preferred compositions of the invention and there are known pharmaceutical forms for such administration, for example tablets, capsules, granules, syrups and aqueous or oily suspensions.

Tablets may be prepared from a mixture of the active compound with fillers such as lactose or calcium phosphate, disintegrating agents, for example maize starch, lubricating agents, for example magnesium stearate, binders for example microcrystalline cellulose or polyvinyl pyrrolidone and other optional ingredients known in the art to permit tableting the mixture by known methods. The tablets may, if desired, be coated using known methods and excipients which may include enteric coating using for example hydroxypropylmethyl-cellulose phthalate. The tablets may be formulated in a manner known to those skilled in the art so as to give a sustained release of the compounds of the present invention. Such tablets may, if desired, be provided with enteric coatings by known methods, for example by the use of cellulose acetate phthalate.

Similarly, capsules, for example hard or soft gelatin capsules, containing the active compound with or without added excipients, may be prepared by known methods and, if desired, provided with enteric coatings in a known manner. The tablets and capsules may conveniently each contain 0.1 to 1000 mg (for example 10 mg, 50 mg, 100 mg, 200 mg, 400 mg, 600 mg or 800 mg) of the active compound. Other compositions for oral administration include, for example, aqueous suspensions containing the active compound in an aqueous medium in the presence of a non-toxic suspending agent such as sodium carboxymethylcellulose, and oily suspensions containing a compound of the present invention in a suitable vegetable oil, for example sunflower oil.

The active compound may be formulated into granules with or without additional excipients. The granules may be ingested directly by the patient or they may be added to a suitable liquid carrier (for example water) before ingestion. The granules may contain disintegrants (for example a pharmaceutically acceptable effervescent couple formed from an acid and a carbonate or bicarbonate salt) to facilitate dispersion in the liquid medium.

Compositions for topical administration are also preferred compositions of the invention. The pharmaceutically active compound may be dispersed in a pharmaceutically acceptable cream, ointment or gel. A suitable cream may be prepared by incorporating the active compound in a topical vehicle such as petrolatum and/or light liquid paraffin, dispersed in an aqueous medium using surfactants. An ointment may be prepared by mixing the active compound with a topical vehicle such as a mineral oil, petrolatum and/or a wax e.g. paraffin wax or beeswax. A gel may be prepared by mixing the active compound with a topical vehicle comprising a gelling agent e.g. basified Carbomer BP, in the presence of water. Topically administrable compositions may also comprise a matrix in which the pharmaceutically active compounds of the present invention are dispersed so that the compounds are held in contact with the skin in order to administer the compounds transdermally. A suitable transdermal composition may be prepared by mixing the pharmaceutically active compound with a topical vehicle, such as described above, together with a potential transdermal accelerant such as dimethyl sulphoxide or propylene glycol.

Compositions of the invention suitable for rectal administration are known pharmaceutical forms for such administration, for example suppositories with hard fat, synthetic glycerides or polyethylene glycol bases.

Compositions of the invention suitable for parenteral administration are known pharmaceutical forms for such administration, for example sterile suspensions or sterile solutions in a suitable solvent.

Compositions of the invention suitable for inhalation via the mouth and/or the nose are the known pharmaceutical forms for such administration, for example aerosols, nebulised solutions or powders. Metered dose systems, known to those skilled in the art, may be used.

Compositions suitable for application to the buccal cavity include slow dissolving tablets, troches, chewing gum, gels, pastes, powders, mouthwashes or rinses.

The compounds of the present invention may also be administered by continuous infusion either from an external source, for example by intravenous infusion, or from a source of the compound placed within the body. Internal sources include implanted reservoirs containing the compound to be infused which is continuously released for example by osmosis and implants which may be a) liquid such as an oily solution or suspension of the compound to be infused for example in the form of a very sparingly water-soluble derivative such as a dodecanoate salt or b) solid in the form of an implanted support for example of a synthetic resin of waxy material for the compound to be infused. The support may be a single body containing all the compound or a series of several bodies each containing part of the compound to be delivered.

In some formulations it may be beneficial to use the compounds of the present invention in the form of particles of very small size, for example as obtained by fluid energy milling.

In the compositions of the present invention the active compound may, if desired, be associated with other compatible pharmacologically active ingredients, for example, a non-steroidal antiinflammatory agent e.g. ibuprofen, S(+)-ibuprofen, flurbiprofen or S(+)-flurbiprofen, an analgesic or an antipyretic agent.

The compounds of formula I are indicated for use as medicaments. In particular compounds of formula I are indicated for use as anti-rheumatic agents by their activity demonstrated by means of tests on standard laboratory animals. Such tests include, for example, the oral administration of compounds of formula I to mice with experimental antigen-induced arthritis. Compounds of formula I are suitable for use in treating rheumatic diseases for example rheumatoid arthritis, osteoarthritis, osteoporosis, crystal arthropathies (e.g. gout), reactive arthritis, ankylosing spondylitis or psoriatic arthropathy. It is believed that compounds of formula I and pharmaceutically acceptable salts thereof are disease-modifying antirheumatic agents.

The compounds of formula I are also indicated for use as immunomodulatory agents, and are generally immunosuppressants. The compounds according to the invention are useful in the treatment of diseases resulting from an aberrant immune reaction. Thus the pharmaceutical compositions containing a therapeutically effective amount of a compound of formula I may be used to treat diseases with an immunological association. The compounds are also useful to treat immunologically-induced diseases including allergic and inflammatory conditions, particularly those mediated by the release of cytokines such as tumour necrosis factor (TNF).

The immunomodulatory activity of compounds falling within formula I may be demonstrated by means of in vitro and in vivo tests. Such tests include, for example, in vitro and/or in vivo tests which detect the production of inflammatory cytokines e.g. TNF, in response to endotoxins. Thus, compounds of formula I are useful as modulators of cytokine synthesis, immunomodulatory agents, anti-inflammatory agents and anti-allergic agents.

Diseases which may be treated by compounds according to the present invention include immunologically based diseases such as transplant rejection, eg kidney rejection; and graft-versus-host disease; joint inflammation; autoimmune diseases, such as thyroiditis, type 1 diabetes, multiple sclerosis, cerebral inflammation, sarcoidosis and systemic lupus erythematosus; cutaneous disorders, such as contact sensitivity, eczema and psoriasis; respiratory disorders for example: asthma and rhinitis; gastrointestinal disorders for example: gastritis, Crohn's disease, ulcerative colitis and other inflammatory diseases of the bowel; diseases of the oral cavity for example: periodontitis and gingivitis; HIV infection (AIDS); septic shock; malaria; cerebral inflammation; viral diseases; neoplasia and cachexia. Other diseases which may also be treated by compounds of the present invention include muscle trauma, gout, tendonitis and bursitis; Alzheimer's disease; cutaneous disorders for example: urticaria, allergic skin diseases, burns, occular inflammation and iritis.

Compounds of formula I may also be suitable for the treatment of diseases of the oral cavity for example periodontitis, gingivitis and alveolar bone resorption.

Accordingly, in a further aspect, the present invention also includes a method of treating rheumatic diseases, particularly rheumatoid arthritis and osteo-arthritis, comprising the administration of a therapeutically effective amount of a compound of formula I including pharmaceutically acceptable salts thereof to a mammal in need thereof.

Accordingly, in another aspect, the present invention also includes a method of treating diseases with an immunological association in a mammal in need of such treatment, comprising the administration of a therapeutically effective amount of a compound of formula I to said mammal.

Compounds of formula I may also be administered in a prophylactic manner to mammals, particularly humans who have been identified as being susceptible to arthritic diseases.

Whilst the precise amount of active compound administered will depend on a number of factors, for example the age of the patient, the severity of the condition and the past medical history and always lies within the sound discretion of the administering physician, a suitable dose for oral administration to mammals, including humans, is generally within the range 0.01–80 mg/kg/day, more usually 0.2–40 mg/kg/day given in single or divided doses. For parenteral administration, a suitable dose is generally within the range 0.001–80 mg/kg/day, more usually 0.2–40 mg/kg/day given in single or divided doses or by continuous infusion. A suitable preparation for topical administration generally contains the active ingredient within the range 0.01–20% by weight, more usually 0.05–5% by weight. Oral administration is preferred.

The pharmaceutical compositions containing a therapeutically effective amount of a compound of formula I may be used to treat rheumatic diseases such as rheumatoid arthritis and osteoarthritis. In such treatment the amount of the compound of formula I administered per day is in the range 0.1 to 6000 mg.

In yet another aspect, the present invention provides the use of a compound of formula I in the manufacture of a medicament for use in the treatment of rheumatic diseases such as rheumatoid arthritis and osteoarthritis.

The present invention also includes a method of treating inflammatory and/or allergic conditions in a mammal in need of such treatment comprising the administration of a therapeutically effective amount of a compound of formula I to said mammal.

In yet another aspect the present invention provides the use of a compound of formula I in the manufacture of a medicament for use in the treatment of inflammatory diseases, allergic conditions or diseases with an immunological association.

Processes for the preparation of compounds of formula I will now be described. These processes form a further aspect of the present invention. The processes listed are preferably carried out at atmospheric pressure unless otherwise stated.

Compounds of formula I may be prepared by cyclising a compound of formula III

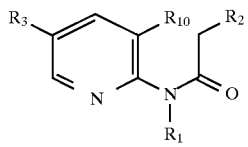

III in which $R_1$, $R_2$ and $R_3$ are as previously defined and $R_{10}$ represents cyano or a group of formula $COR_{11}$ in which $R_{11}$ represents a leaving group, for example halo, a $C_{1-6}$ alkoxy group, an aryloxy group, an arylalkoxy group, a $C_{1-6}$ alkanoyloxy group, a ($C_{1-6}$ alkoxy)carbonyloxy group, an amino group of formula $NR_{12}R_{13}$ (in which $R_{12}$ and $R_{13}$ independently represent hydrogen or a $C_{1-6}$ alkyl group or $R_{12}$ and $R_{13}$ together with the nitrogen atom to which they are attached represent a saturated 3–7 membered heterocyclic ring optionally containing sulphur, oxygen or an additional nitrogen atom, wherein the ring is optionally substituted by one or more $C_{1-4}$ alkyl groups), in the presence of a base, for example sodium hydride or sodium ethoxide, in the presence of an inert organic liquid which is preferably a solvent for the compound of formula III, for example ethanol, tetrahydrofuran or N,N-dimethylformamide, at a temperature in the range −50° to 250° C., preferably in the range −15° to 150° C., optionally followed by hydrolysis when $R_{10}$ represents cyano or an amide group and optionally followed by acidification.

Compounds of formula I may be prepared by cyclising a compound of formula IV

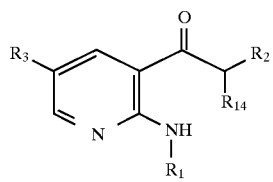

IV in which $R_1$, $R_2$ and $R_3$ are as previously defined and $R_{14}$ represents a group of formula $COR_{11}$ in which $R_{11}$ is as previously defined, for example by heating, at a temperature in the range 30–250° C. preferably in the presence of an inert organic liquid which is preferably a solvent for the compound of formula IV, for example N,N-dimethylformamide.

Compounds of formula I may be prepared by condensing a compound of formula V

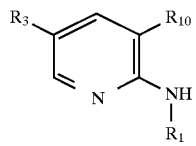

V in which $R_1$, $R_3$ and $R_{10}$ are as defined previously with a compound of formula VI

$R_2CH_2R_{14}$    VI in which $R_2$ is as previously defined and $R_{14}$ represents a group of formula $COR_{11}$ in which $R_{11}$ is as previously defined, for example by reacting together at a temperature in the range 0–150° C., preferably in the presence of a base, for example sodium ethoxide, in the presence of an inert organic liquid which is preferably a solvent for the reactants, for example N,N-dimethyl-formamide, and then reacting at a temperature in the range 0–250° C., optionally followed by hydrolysis when $R_{10}$ represents cyano or an amide group and optionally followed by acidification. Preferably $R_{14}$ is the same as group $R_2$.

Compounds of formula I may be prepared by reacting a compound of formula VII

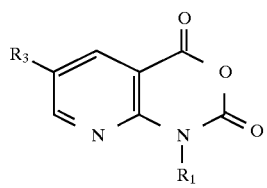

VII in which $R_1$ and $R_3$ are as previously defined with a compound of formula VI

$R_2CH_2R_{14}$    VI in which $R_2$ is as previously defined and $R_{14}$ represents a group of formula $COR_{11}$ in which $R_{11}$ is as previously defined, for example by reacting together at a temperature in the range 0–150° C., preferably in the presence of a base, for example sodium hydride, in the presence of an inert organic liquid which is preferably a solvent for the reactants, for example N,N-dimethyl-formamide, and then reacting at a temperature in the range 0–250° C., optionally followed by acidification. Preferably $R_{14}$ is the same as group $R_2$.

Compounds of formula I may be prepared by cyclising a compound of formula IX

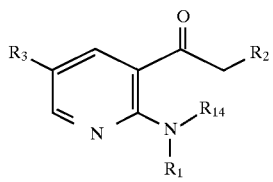

in which $R_1$, $R_2$, $R_3$ and $R_{14}$ are as previously defined, optionally in the presence of a base, for example sodium hydride, preferably in the presence of an organic liquid which is preferably a solvent for the compound of formula IX, for example N,N-dimethylformamide, at a temperature in the range 0–150° C. optionally followed by acidification.

Compounds of formula I may be prepared by reacting a compound of formula XIII

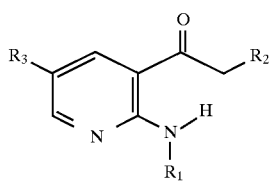

in which $R_1$, $R_2$ and $R_3$ are as previously defined with a compound of formula $Y_1COY_2$ in which $Y_1$ represents halo, alkoxy (optionally substituted by halo), aryloxy, arylalkoxy, cyano or a group of formula $NR_{15}R_{16}$ (in which $R_{15}$ and $R_{16}$ independently represent a $C_{1-6}$ alkyl group or $R_{15}$ and $R_{16}$ together with the nitrogen atom to which they are attached represent a saturated 3–7 membered heterocyclic ring) and $Y_2$ represents halo, alkoxy (optionally substituted by halo), aryloxy or arylalkoxy (for example $Y_1COY_2$ is ethyl chloroformate or diethyl carbonate), optionally in the presence of a base, for example sodium hydride or triethylamine, preferably in the presence of an inert organic liquid which is preferably a solvent for the compound of formula XIII, for example N,N-dimethylformamide, at a temperature in the range 0–150° C.

Compounds of formula I may be prepared by reacting a compound of formula XII

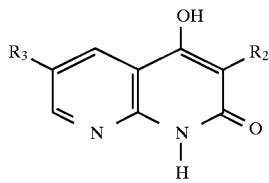

in which $R_2$ and $R_3$ are as previously defined, with an alkylating agent of formula $R_1X$ in which $R_1$ is as previously defined and X represents a leaving group, for example chloro, bromo or iodo. It will be appreciated by those skilled in the art that an O-alkylated or an O,N-dialkylated product may be obtained in this process from which the desired compound may be obtained by chromatography. The undesired O,N-dialkylated product may be converted into the N-alkylated product by methods known to those skilled in the art, e.g. by hydrolysis. Alternatively the O-alkylated product may be converted into the N-alkylated product by heating.

Compounds of formula III may be prepared by reacting a compound of formula V with a compound of formula VI at a temperature in the range −50° to 150° C., preferably in the presence of an organic liquid which is preferably a solvent for the compound of formula V.

Compounds of formula IV may be prepared by reacting a compound of formula V with a compound of formula VI in the presence of a base, for example sodium hydride or sodium ethoxide, in the presence of an organic liquid, preferably a solvent for compounds of formula V, at a temperature in the range −50° to 150° C.

Compounds of formula IV may also be prepared by reacting a compound of formula VII with a compound of formula VI in the presence of a base, for example sodium hydride or sodium ethoxide, in the presence of an organic liquid, preferably a solvent for compounds of formula V, at a temperature in the range −50° to 150° C.

Compounds of formulae V, VI, and VII may be prepared by methods known to those skilled in the art.

Compounds of formula IX may be prepared by reacting a compound of formula X

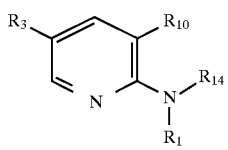

in which $R_1$, $R_3$, $R_{10}$ and $R_{14}$ are as defined previously with a compound of formula XI $$(R_2CH_2)_nM_1 \qquad XI$$

in which $R_2$ is as previously defined and when n is 1 then $M_1$ represents Li or MgX, in which X represents bromo, chloro or iodo, and when n is 2 then $M_1$ represents Cd, optionally in the presence of a transition metal or a transition metal salt, by methods known to those skilled in the art, optionally followed by hydrolysis when $R_{10}$ represents cyano or an amide group and optionally followed by acidification.

Compounds of formula X and XI may be prepared by methods known to those skilled in the art. For example, compounds of formula X may be prepared from compounds of formula V.

Compounds of formula XII may be prepared by methods analogous to those described for the preparation of compounds of formula I by reaction of compounds of formulae III, IV, V, VII and IX in which $R_1$ represents hydrogen.

Compounds of formula XIII may be prepared by reacting a compound of formula V with a compound of formula XI in an analogous manner to the preparation of compounds of formula IX.

Certain intermediate compounds of formulae III, IV, V, VII, IX, X and XII are believed to be novel. All novel compounds herein form a further aspect of the invention.

The therapeutic activity of the compounds of the present invention has been demonstrated by tests which include the oral administration of the compounds to mice with experimental antigen-induced arthritis. The compounds showed activity in the following test.

Experimental Antigen-induced Arthritis Test

Female BALB/c mice, 8 weeks of age were used: each control group contained either 35, 60 or 80 mice and each test group contained either 13, 15 or 20 mice respectively. The mice were sensitised by subcutaneous injection into the flank or nuchal area with an emulsion (0.1 ml) consisting of a solution of methylated bovine serum albumin (m-BSA) (0.1 mg) in sterile aqueous sodium chloride solution (0.05 ml; 0.15M) and Freund's Complete Adjuvant (0.05 ml) containing, in total, killed *Mycobacterium tuberculosis* (0.075 mg). Simultaneously each mouse was injected intra-peritoneally with an aqueous suspension of heat killed *Bordetella pertussis* (0.05 ml; $2\times10^9$ organisms). Identical injections were administered after 7 days. After a further 14 days the left knee-joint of each mouse was injected with a solution of m-BSA (0.1 mg) in aqueous sodium chloride solution (0.01 ml; 0.15M) (intra-articular challenge). This procedure induced a chronic erosive arthritis restricted to the challenged joint.

The test compounds were suspended in a vehicle of aqueous carboxymethyl cellulose solution (0.25% w/v) containing TWEEN®80 (1.5% w/v) at varying dosages and 0.1 ml was administered to each test mouse by gastric intubation. The control mice received the vehicle with no test compound. Administration occurred daily for 28 days commencing 14 days after intra-articular challenge. After 42 days the test was terminated and the animals were killed using a rising concentration of carbon dioxide and the arthritic hind leg removed.

The femur and tibia were cut midway along their length and the knee-joint trimmed free of skin and musculature. The arthritic joints were placed in perforated plastic holders and fixed in 10% formol saline for at least 48 hours. They were then decalcified in 5% formic acid for 72 hours with constant agitation (replacing the formic acid after the first 24 hours), washed in water, dehydrated in alcohol and embedded in paraffin wax. The joints were sectioned in the sagittal plane at 5 $\mu$m and stained with Van Gieson's stain. Each joint was sectioned at two levels.

The severity of arthritis was assessed by examination of the prepared sections. Synovitis and pannus formation were graded on a 0–5 scale, by a skilled operator, according to the degree of synovial lining cell hypertrophy and hyperplasia, infiltration of the synovium by lymphocytes, plasma cells, monocytes/macrophages, fibroblasts and polymorpho-nuclear (PMN) leukocytes and the degree of pannus formation. Erosions of cartilage and bone were also graded on a 0–5 scale, by a skilled operator, the score reflecting the proportion of articular surface eroded as well as the depth of the erosions. Using the combined data the drug effects were expressed as the percentage change in the mean scores for synovitis and erosions compared to those of the control group. The data were then analysed using the Mann-Whitney U-test.

Those compounds which induced a statistically significant suppression of erosions or synovitis at a dosage of 30 mg/kg or below were deemed to be active. The results obtained are given in the Examples. Preferred compounds induce a statistically significant suppression of erosions.

The therapeutic activity of compounds of formula I (in particular their ability as immunomodulants) was demonstrated by activity of certain compounds of formula I (those compounds so tested referred to hereinafter as Test Compounds) in the mouse tumour necrosis factor-$\alpha$ (TNF-$\alpha$) test (hereinafter referred to as the MTNF Test).

Mouse Tumour Necrosis Factor-$\alpha$ Test

The therapeutic activity of Test Compounds was demonstrated in an in vivo test which determined the ability of the Test Compounds to inhibit the release of TNF-$\alpha$ in response to the administration of endotoxin. TNF-$\alpha$ is currently thought to be a key mediator in the pathogenesis of a number of autoimmune and inflammatory diseases and its inhibition is a potentially beneficial pharmacological goal. The MTNF Test is similar to that described by Zuckerman and Bendele (1989), Infection and Immunity, Vol 57 (10), pages 3009–3013. The MTNF Test was carried out as described below.

Six week old, barrier-reared female mice of the BALB/c strain were obtained from Harlan-Olac Ltd and maintained under semi-barrier conditions with free access to food (CRM diet) and water for one to three weeks before use. The Test Compound was combined with a carrier of 100 $\mu$l of a solution of 1.5% v/v sorbitan esters (available commercially under the trade name Tween 80) and 0.25% v/v cellosize in sterile water. The Test Compound in the carrier was administered orally to four BALB/c mice (hereinafter referred to as the Test Mice). The concentration of the Test Compound was such as to provide dosages of Test Compound selected from 100 mg/kg, 30 mg/kg, 10 mg/kg, 3 mg/kg, 1 mg/kg, 0.1 mg/kg and 0.03 mg/kg. An endotoxin, (lipopolysaccharide) (hereinafter referred to as LPS) was purified from *Escherichia coli* serotype 0127:B8 (obtained from Sigma [Code L3137]). A solution of LPS at a concentration of 0.5 mg/ml in sterile endotoxin free 0.9% saline (obtained from Flowfusor) was prepared. Two hours after the administration of the Test Compound, 0.2 ml of the LPS solution was administered intraperitoneally to each of the Test Mice. A control group of eight BALB/c mice (hereinafter referred to as the Control Mice) were treated in a similar manner to that described above for the Test Mice except that no Test Compound was included with the carrier. One hour after administration of LPS to the Control Mice and Test Mice, they were killed by rising concentration of $CO_2$ and blood samples were collected by cardiac puncture.

The blood was allowed to clot at room temperature for one hour and the serum was separated from the clotted blood following centrifugation. The serum was stored at $-35°$ C. until assay. Serum from individual mice at a dilution of 1:4 was assayed for TNF-$\alpha$ concentration by the enzyme linked immunosorbant assay (hereinafter referred to as ELISA) which was carried out as follows. Each well in a vinyl assay plate containing 96 wells (from Costar) was coated with 50 $\mu$l of 2 $\mu$g/ml hamster anti-mouse TNF-($\alpha$ and $\beta$) monoclonal antibody in a 0.1M sodium hydrogen carbonate buffer at pH 8.2 and the plate was left overnight at 4° C. The plate was then washed with a wash buffer (comprising phosphate buffered saline [hereinafter known as PBS] with 0.05% v/v of the sorbitan ester available commercially under the trade name Tween 20). Then a 200 $\mu$l aliquot of a blocking/dilution buffer (comprising 10% sheep serum in PBS with 0.1% v/v of the Tween 20 sorbitan ester) was added to each well and the plate was incubated at 37° C. for 30 minutes. After aspirating the blocking buffer, the murine serum samples diluted 1:4 in the blocking/dilution buffer, or (as standards) purified recombinant murine TNF-$\alpha$ (obtained from Genzyme) at a range of concentrations, were added to duplicate wells and the plate was incubated at 37° C. for a further two hours. The plate was washed with the wash buffer and 100 $\mu$l of a rabbit antibody solution (comprising a 1 in 10,000 dilution of a polyclonal rabbit anti-mouse TNF-$\alpha$ antibody in the blocking/dilution buffer [prepared as above]) was added to each well and incubated for a further 1 hour 30 minutes at 37° C. The plate was washed again and then 100 $\mu$l of an anti-rabbit IgG peroxidase conjugate (obtained from Binding Site) at a 1 in 4000 dilution was added to each well, and the plate was incubated at 37° C. for 30 minutes. After further washing of the plate, 100 $\mu$l of a substrate solution was added to each well (the substrate solution comprised 0.1 mg/ml 3,3',5,5'-tetramethylbenzidine dihydrochloride buffered to pH 5.0 with a 0.1M phosphate citrate buffer, to which 2 μl of 30% hydrogen peroxide per 10 ml was added just before use). The colour of the solution in each well was allowed to develop. The reaction was stopped by the addition of 25 μl of 1M sulphuric acid and the optical density of the solution in each well read in a multichannel spectrophotometer at 450 mm.

The concentration (expressed as ng/ml) of TNF-α in the serum collected from each of the Test Mice was compared with that in the serum of each of the Control Mice. The mean TNF-α serum concentration of the Test Mice and the Control Mice was determined by comparison with a standard curve. The significance of the percentage change of mean TNF-α serum concentration between the Test Mice and Control Mice was determined by one-way analysis of variance followed by a two-tailed multiple t-test. A reduction in serum TNF-α concentration between the Test Mice and Control Mice indicated that the Test Compound inhibited the release of mouse TNF-α, and thus had activity as an immunosuppressant. Test Compounds which caused a statistically significant percentage reduction of >35% in mean serum TNF-α concentration at a single dose of the Test Compound of 100 mg/kg or less were considered active in the MTNF Test. The lowest dose (minimum effective dose [MED]) for which activity was found was determined for each Test Compound. The results are given in the Examples.

The invention is illustrated by the following non-limitative Examples in which parts and percentages are by weight and compositions of mixed solvents are given by volume. Novel compounds were characterised by elemental analysis and one or more of the following spectroscopic techniques: nuclear magnetic resonance, infra-red and mass spectroscopy.

In the Examples the following abbreviations are used: IMS=industrial methylated spirit and DMF=N,N-dimethylformamide.

Unless otherwise stated, the starting materials used in the Examples are commercially available and may be obtained by reference to the Fine Chemicals Directory.

EXAMPLE 1 a) A mixture of 2-chloronicotinic acid (10.0 g) and benzylamine (13.34 ml) was heated at 130° C. for 2 hours. The mixture was cooled and the resulting solid was broken up, triturated with water, acidified to pH 6 and filtered. The solid obtained was boiled up in IMS (200 ml), cooled and filtered to give 2-benzylaminonicotinic acid, m.p. 223°–225° C.

b) Chlorine gas was bubbled through a suspension of the product from a) (13.70 g) in glacial acetic acid (370 ml) at ambient temperature for 5 hours with stirring. The mixture was stirred at ambient temperature for 18 hours and then diluted with ether (100 ml). The mixture was filtered to give 2-benzylamino-5-chloronicotinic acid hydrochloride, m.p. 210°–212° C.

c) Chloroacetonitrile (2.9 ml) was added dropwise with stirring to a solution of the product from b) (12.0 g), triethylamine (10.9 ml) and acetone (90 ml) at 0° C. The mixture was stirred and boiled under reflux for 18 hours and then hot filtered. The filtrate was evaporated under reduced pressure to give an oil which was dissolved in dichloromethane, washed with water, dried and evaporated to give cyanomethyl 2-benzylamino-5-chloronicotinate as an oil.

d) A mixture of the product from c) (11.40 g), triethylamine (1.5 ml) and methanol (150 ml) was boiled under reflux for 15 hours. The mixture was cooled and filtered to give methyl 2-benzylamino-5-chloronicotinate, m.p. 77°–79° C.

e) Ethyl malonyl chloride (3.5 ml) was added dropwise with stirring to a solution of the product from d) (6.80 g), triethylamine (3.8 ml) and ether (260 ml) at ambient temperature. The resultant mixture was stirred at ambient temperature for 2 hours and then filtered. The filtrate was evaporated under reduced pressure to give a residue which was dissolved in ethanol (50 ml) with warming. This solution was added rapidly, dropwise, to a solution of sodium (1.14 g) in ethanol (150 ml) with stirring. The mixture was stirred for 30 minutes at ambient temperature and then poured into cold water (300 ml). This mixture was acidified with concentrated hydrochloric acid, stirred for 1 hour at ambient temperature and then filtered to give a solid which was washed with water and then with petrol. The solid was triturated with ether and filtered to give ethyl 1-benzyl-6-chloro-4-hydroxy-2-oxo-1,2-dihydro-1,8-naphthyridine-3-carboxylate, m.p. 141°–142° C.

Active 2/2 at 10 mg/kg in the Mouse Arthritis Test. Active at ≦1 mg/kg in the Mouse TNF-α Test.

EXAMPLE 2

This was carried out in a similar manner to Example 1.

a) 2-Benzylaminonicotinic acid was converted into methyl-2-benzylaminonicotinate (b.p. 162°–164° C. at 1 mbar) using the method described in Example 1 parts c) and d) with the exception that the product was distilled.

b) Ethyl 1-benzyl-4-hydroxy-2-oxo-1,2-dihydro-1,8-naphthyridine-3-carboxylate, m.p. 121°–123° C., was prepared by reacting methyl-2-benzylaminonicotinate (6.0 g) and ethyl malonyl chloride (3.5 ml) in ether (260 ml) containing triethylamine (3.8 ml) and then adding the residue obtained on work up dissolved in ethanol (50 ml) to a solution of sodium (1.14 g) in absolute ethanol (150 ml).

Active 2/2 at 30 mg/kg; and Active 1/1 at 10 mg/kg in the Mouse Arthritis Test.

EXAMPLE 3 a) A mixture of 2-chloronicotinic acid (30.0 g) and 4-chlorobenzylamine (45 ml) was heated at 120° C. for 3.5 hours. The mixture was cooled to ambient temperature and the solid obtained was washed with water and collected by filtration. The solid was boiled in methanol and filtered to give 2-(4-chlorobenzylamino)-nicotinic acid, m.p. 240°–242° C.

b) Thionyl chloride (45 ml) was added dropwise to a mixture of the product from a) (10.00 g) and DMF (2 drops) at ambient temperature. The mixture was stirred at ambient temperature for 18 hours and then excess thionyl chloride was removed under reduced pressure. Methanol (40 ml) was added to the residue and the mixture was stirred at ambient temperature for 4 hours and then boiled under reflux for 2 hours. The mixture was cooled to ambient temperature and the methanol removed under reduced pressure to give a residue which was triturated with ether and filtered to give methyl 2-(4-chlorobenzylamino)nicotinate hydrochloride, m.p. 148°–150° C., which was neutralised with concentrated sodium hydroxide solution and extracted into ethyl acetate to give the free base.

c) A solution ethyl malonyl chloride (3.11 ml) in dichloromethane (11 ml) was added dropwise to a mixture of methyl 2-(4-chlorobenzylamino)nicotinate (5.00 g) and sodium bicarbonate (1.80 g) in dichloromethane (27 ml) at 10° C. under nitrogen. The mixture was boiled under reflux for 6 hours and then left to stand at ambient temperature for 18 hours. The mixture was boiled for a further 6 hours then left to stand at ambient temperature for 64 hours. Water (100 ml) was added and the mixture was stirred at ambient temperature for 45 minutes. The organic layer was separated, washed with 5% hydrochloric acid, then with water, then dried and evaporated to give a residue which was dissolved in ethanol (50 ml) and added dropwise at 10° C. to a solution of sodium (0.58 g) in ethanol (40 ml). The mixture was heated to 95° C. and stirred at this temperature for 30 minutes, then left to stand at ambient temperature for 18 hours. The solvent was removed under reduced pressure and the residue was stirred with 5% hydrochloric acid (250 ml) at 0° C. for 1 hour. The mixture was filtered to give a solid which was recrystallised from ethanol to give ethyl 1-(4-chlorobenzyl)-4-hydroxy-2-oxo-1,2-dihydro-1,8-naphthyridine-3-carboxylate, m.p. 142°–144° C.

EXAMPLE 4 a) A mixture of 2,5-dichloronicotinic acid (30.0 g) and 4-methoxybenzylamine (41.0 ml) was heated at 150° C. under nitrogen for 2 hours. The mixture was cooled to ambient temperature, dissolved in boiling water, acidified to pH 6 and filtered. The collected solid was dried, boiled up with IMS, then filtered to give 5-chloro-2-(4-methoxybenzylamino)nicotinic acid, m.p. 204°–206° C.

b) Triethylamine (10.0 ml) was added dropwise with stirring to a suspension of the product from a) (10.0 g) in acetone (60.0 ml) with cooling. Chloroacetonitrile (2.1 ml) was added dropwise to the resultant solution and the mixture boiled under reflux for 13 hours. The mixture was hot filtered and the residue washed with boiling acetone. The filtrate and washings were combined and evaporated under reduced pressure to give a solid which was stirred with water (250 ml) for 2 hours and then filtered to give cyanomethyl 5-chloro-2-(4-methoxybenzylamino)nicotinate which was used in c) without further purification.

c) A mixture of the product from b) (11.4 g), methanol (50 ml) and triethylamine (1.0 ml) was boiled under reflux for 24 hours under nitrogen. The mixture was cooled to ambient temperature and the solid collected by filtration and recrystallised from ethyl acetate to give methyl 5-chloro-2-(4-methoxybenzylamino)nicotinate, m.p. 75°–77° C.

d) A solution of the product from c) (3.2 g) in 1,4-dioxane (8.0 ml) was added dropwise with stirring to a suspension of sodium hydride (816 mg of a 60% dispersion in mineral oil) in 1,4-dioxane (8.0 ml) at ambient temperature. Ethyl malonyl chloride (1.5 ml) was added and the mixture stirred at ambient temperature for 3 hours. Further ethyl malonyl chloride (1.0 ml) was added and the mixture stirred at ambient temperature for 18 hours. Further ethyl malonyl chloride (0.6 ml) was added, keeping the temperature below 20° C., and the mixture stirred at ambient temperature for a further 21 hours. The mixture was warmed to 45° C. and heated at this temperature for 6 hours. The mixture was cooled to ambient temperature and filtered. Ether was added to the filtrate to precipitate more solid. The solid collected by filtration and that collected by further filtration of the filtrate were combined, dissolved in water and acidified to pH 5. The solid was collected by filtration and dried to give ethyl 6-chloro-4-hydroxy-1-(4-methoxybenzyl)-2-oxo-1,2-dihydro-1,8-naphthyridine-3-carboxylate, m.p. 185°–187° C.

EXAMPLE 5 a) Trimethylsilylazide (89.1 ml) was added dropwise, with stirring, to a suspension of quinolinic anhydride (100.0 g) in dry chloroform (450 ml) under nitrogen. The mixture was stirred until nitrogen evolution had subsided (around 30 minutes) and then boiled under reflux with stirring for 45 minutes to give a solution. The mixture was cooled to ambient temperature and ethanol (40.0 ml) was added. The mixture was stirred for 20 minutes and a precipitate was collected by filtration and dried under vacuum overnight. The solid was stirred in cold acetonitrile (850 ml) and filtered. The filtrate was boiled under reflux for 15 minutes with stirring and then cooled in ice and filtered to give 4H-pyrido[2,3-d] [1,3]oxazine-2,4(1H)-dione, m.p. 213°–215° C. (with decomposition).

b) Sodium hydride (4.02 g of a 60% dispersion in mineral oil) was added in portions to a stirred suspension of the product from a) (15.0 g) in dry dimethylacetamide (250 ml) under nitrogen at 0° C. The mixture was stirred at ambient temperature for 1 hour and then at 65° C. for 0.5 hours. The solution was cooled to ambient temperature and phenethyl bromide (15.0 ml) was added dropwise. The mixture was stirred at ambient temperature under nitrogen for 64 hours and then the solvent removed under reduced pressure to give a viscous oil which was dissolved in dichloromethane (500 ml) and washed with water. The organic layer was separated, dried and evaporated to give a solid which was purified by flash column chromatography on silica using petroleum ether, b.p. 60°–80° C./ethyl acetate 1:1 as the mobile phase to give a yellow solid which was recrystallised from dichloromethane/diethyl ether to give 1-phenethyl-4H-pyrido[2,3-d] [1,3]oxazine-2,4(1H)-dione, m.p. 147°–149° C.

c) A solution of the product from b) (2.00 g) and diethyl malonate (1.20 g) in dry 1,4-dioxane (15 ml) was added to a suspension of sodium hydride (300 mg of a 60% dispersion in mineral oil) in dry 1,4-dioxane (10 ml) which was boiling under reflux under nitrogen with stirring. The mixture was stirred and boiled under reflux for 6 hours. The mixture was cooled to ambient temperature and diluted with ether (100 ml). The mixture was filtered and the collected solid was stirred in water (100 ml) for 1 hour and then filtered. The filtrate was acidified to pH 5 with glacial acetic acid and filtered to give ethyl 4-hydroxy-2-oxo-1-phenethyl-1,2-dihydro-1,8-naphthyridine-3-carboxylate, m.p. 121°–123° C.

PHARMACEUTICAL EXAMPLES

Example U

In the preparation of capsules, 10 parts by weight of active compound and 240 parts by weight of lactose are de-aggregated and blended. The mixture is filled into hard gelatin capsules, each capsule containing 10 mg active compound.

Example V

Tablets are prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch are de-aggregated, blended and the resulting mixture is granulated with a solution of the polyvinylpyrrolidone in ethanol. The dry granulate is blended with magnesium stearate and the rest of the starch. The mixture is then compressed in a tableting machine to give tablets containing 10 mg of active compound.

Example W

Tablets are prepared by the method of the previous Example. The tablets are enteric coated in a conventional manner using a solution of 20% cellulose acetate phthalate and 3% diethyl phthalate in ethanol:dichloromethane (1:1).

Example X

In the preparation of suppositories, 100 parts by weight of active compound is incorporated in 1300 parts by weight of semi-synthetic glycerides as the suppository base and the mixture formed into suppositories each containing 100 mg of active ingredient.

Example Y

In the preparation of capsules, 50 parts by weight of active compound, 300 parts by weight of lactose and 3 parts by weight of magnesium stearate are de-aggregated and blended. The mixture is filled into hard gelatin capsules, each capsule containing 50 mg of active ingredient.

Example Z

The active compound is incorporated into the base by thorough homogenization until the drug is evenly distributed. The ointment is packed into 10 g amber jars with screw-capped lined lids.

Active compound 0.1 g
White soft paraffin to 10 g

We claim:

1. A compound of formula I

[Structure of formula I: pyridine ring with $R_3$ substituent, fused to a 2-oxo ring with OH, $R_2$, and N-$R_1$ groups]

or a pharmaceutically acceptable salt thereof, in which $R_1$ represents a phenyl $C_{1-6}$ alkyl group, wherein the phenyl ring is unsubstituted or is optionally substituted by one or more of the following: halo, a $C_{1-4}$ alkyl group, a $C_{1-4}$ alkoxy group, hydroxy or trifluoromethyl; and the alkyl chain is unsubstituted or is optionally substituted by one or more $C_{1-2}$ alkyl groups;

$R_2$ represents a $C_{2-6}$ alkoxycarbonyl group; and $R_3$ represents halo.

2. A compound according to claim 1, in which $R_1$ represents phenethyl or a benzyl group which is unsubstituted or is optionally substituted in the phenyl ring by one or more of the following: a $C_{1-4}$ alkoxy group or halo; $R_2$ represents a $C_{2-4}$ alkoxycarbonyl group and $R_3$ represents halo.

3. A compound according to claim 1 selected from the group consisting of ethyl 1-benzyl-6-chloro-4-hydroxy-2-oxo-1,2-dihydro-1,8-naphthyridine-3-carboxylate; and ethyl 6-chloro-4-hydroxy-1-(4-methoxybenzyl)-2-oxo-1,2-dihydro-1,8-naphthyridine-3-carboxylate.

4. A process to prepare a compound of formula I as claimed in claim 1 comprising:

a) cyclising a compound of formula III

[Structure III]

in which $R_1$, $R_2$ and $R_3$ are as previously defined and $R_{10}$ represents cyano or a group of formula $COR_{11}$ in which $R_{11}$ represents a leaving group, in the presence of a base, in the presence of an inert organic liquid at a temperature in the range −50° to 250° C., optionally followed by hydrolysis when $R_{10}$ represents cyano or an amide group and optionally followed by acidification; or b) cyclising a compound of formula IV

[Structure IV]

in which $R_1$, $R_2$ and $R_3$ are as previously defined and $R_{14}$ represents a group of formula $COR_{11}$ in which $R_{11}$ is as previously defined, at a temperature in the range 30°–250° C.; or c) condensing a compound of formula V

[Structure V]

in which $R_1$, $R_3$ and $R_{10}$ are as defined previously with a compound of formula VI $$R_2CH_2R_{14} \quad \text{VI}$$

in which $R_2$ is as previously defined and $R_{14}$ represents a group of formula $COR_{11}$ in which $R_{11}$ is as previously defined, by reacting together at a temperature in the range 0°–150° C., in the presence of a base, in the presence of an inert organic liquid and then reacting at a temperature in the range 0°–250° C., optionally followed by hydrolysis when $R_{10}$ represents cyano or an amide group and optionally followed by acidification; or d) reacting a compound of formula VII

[Structure VII]

in which $R_1$ and $R_3$ are as previously defined with a compound of formula VI $$R_2CH_2R_{14} \quad \text{VI}$$

in which $R_2$ is as previously defined and $R_{14}$ represents a group of formula $COR_{11}$ in which $R_{11}$ is as previously defined, by reacting together at a temperature in the range 0°–150° C., in the presence of a base, in the presence of an inert organic liquid, and then reacting at a temperature in the range 0°–250° C., optionally followed by acidification; or e) cyclising a compound of formula IX

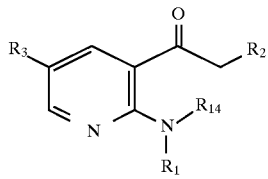

IX in which $R_1$, $R_2$, $R_3$ and $R_{14}$ are as previously defined, optionally in the presence of a base, in the presence of an organic liquid at a temperature in the range 0°–150° C. optionally followed by acidification; or f) compounds of formula I may be prepared by reacting a compound of formula XIII

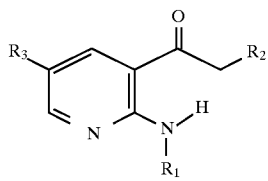

XIII in which $R_1$, $R_2$ and $R_3$ are as previously defined with a compound of formula $Y_1COY_2$ in which $Y_1$ represents halo, alkoxy (optionally substituted by halo), aryloxy, arylalkoxy, cyano or a group of formula $NR_{15}R_{16}$ (in which $R_{15}$ and $R_{16}$ independently represent a $C_{1-6}$ alkyl group or $R_{15}$ and $R_{16}$ together with the nitrogen atom to which they are attached represent a saturated 3–7 membered heterocyclic ring) and $Y_2$ represents halo, alkoxy (optionally substituted by halo), aryloxy or arylalkoxy (for example $Y_1COY_2$ is ethyl chloroformate or diethyl carbonate), optionally in the presence of a base, in the presence of an inert organic liquid, at a temperature in the range 0°–150° C.; or g) reacting a compound of formula XII

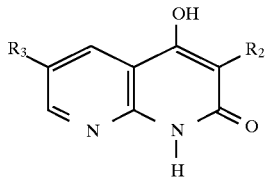

XII in which $R_2$ and $R_3$ are as previously defined, with an alkylating agent of formula $R_1X$ in which $R_1$ is as previously defined and X represents a leaving group.

5. A pharmaceutical composition comprising a therapeutically effective amount of the compound defined in claim 1 together with a pharmaceutically acceptable diluent or carrier.

6. A method of treating diseases with an immunological association comprising administering to a mammal in need of such treatment a therapeutically effective amount of a compound of formula I, as defined in claim 1.

7. A method of treating a rheumatic disease which comprises administering to a mammal suffering from the rheumatic disease a therapeutically effective amount of a compound of formula I

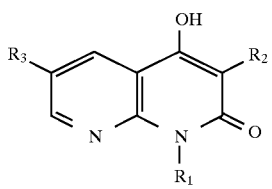

I or a pharmaceutically acceptable salt thereof, in which $R_1$ represents a phenyl $C_{1-6}$ alkyl group in which the phenyl ring is unsubstituted or optionally substituted by one or more of the following: halo, a $C_{1-4}$ alkyl group, a $C_{1-4}$ alkoxy group, hydroxy or trifluoromethyl and the alkyl chain is unsubstituted or optionally substituted by one or more $C_{1-2}$ alkyl groups;

$R_2$ represents a $C_{2-6}$ alkoxycarbonyl group; and $R_3$ represents hydrogen or halo.

* * * * *

UNITED STATES PATENT AND TRADEMARK OFFICE
CERTIFICATE OF CORRECTION

PATENT NO.: 5,854,257

DATED: December 29, 1998

INVENTOR(S): ARMITAGE et al.

It is certified that error appears in the above-identified patent and that said Letters Patent is hereby corrected as shown below:

Col. 17, claim 3, line 62, "1 -benzyl-6-chloro4" should be --1-benzyl-6-chloro-4--.

Signed and Sealed this

Fourth Day of May, 1999

Attest:

Q. TODD DICKINSON

Attesting Officer

Acting Commissioner of Patents and Trademarks